US012589067B2

(12) United States Patent
Barnes et al.

(10) Patent No.: US 12,589,067 B2
(45) Date of Patent: Mar. 31, 2026

(54) COMPOSITION AND METHODS FOR ACTIVATING CELLULAR SIGNALING GENES IN INNATE INFLAMMATORY PATHWAYS

(71) Applicant: LifeVantage Corporation, Lehi, UT (US)

(72) Inventors: Elisa Diane Barnes, Draper, UT (US); Christina Beer, Salt Lake City, UT (US)

(73) Assignee: LIFEVANTAGE CORPORATION, Lehi, UT (US)

( * ) Notice: Subject to any disclaimer, the term of this patent is extended or adjusted under 35 U.S.C. 154(b) by 354 days.

(21) Appl. No.: 18/329,003

(22) Filed: Jun. 5, 2023

(65) Prior Publication Data

US 2024/0398693 A1 Dec. 5, 2024

(51) Int. Cl.

| | |
|---|---|
| *A61K 8/9794* | (2017.01) |
| *A61K 8/65* | (2006.01) |
| *A61K 8/9789* | (2017.01) |
| *A61K 36/21* | (2006.01) |
| *A61K 36/28* | (2006.01) |
| *A61K 36/68* | (2006.01) |
| *A61K 36/81* | (2006.01) |
| *A61K 36/82* | (2006.01) |
| *A61K 36/9066* | (2006.01) |
| *A61K 38/39* | (2006.01) |
| *A61K 45/06* | (2006.01) |
| *A61Q 19/08* | (2006.01) |

(52) U.S. Cl.
CPC .............. *A61K 8/9794* (2017.08); *A61K 8/65* (2013.01); *A61K 8/9789* (2017.08); *A61K 36/21* (2013.01); *A61K 36/28* (2013.01); *A61K 36/68* (2013.01); *A61K 36/81* (2013.01); *A61K 36/82* (2013.01); *A61K 36/9066* (2013.01); *A61K 38/39* (2013.01); *A61K 45/06* (2013.01); *A61Q 19/08* (2013.01); *A61K 2800/522* (2013.01); *A61K 2800/92* (2013.01)

(58) Field of Classification Search
CPC .... A61K 8/9784; A61K 19/08; A61K 8/9789; A61K 8/65; A61K 36/21; A61K 36/28; A61K 36/68; A61K 36/81; A61K 36/82; A61K 36/9066; A61K 38/1706; A61K 38/39; A61K 45/06; A61K 2300/00; A61K 2800/522; A61K 2800/92; A23L 33/18; A23L 33/105
See application file for complete search history.

(56) References Cited

U.S. PATENT DOCUMENTS

| | | | |
|---|---|---|---|
| 8,435,574 B2 | 5/2013 | Myhill et al. | |
| 11,484,563 B2 * | 11/2022 | Dixon et al. ....... | A61K 36/9066 424/729 |
| 2005/0226942 A1 | 10/2005 | Myhill et al. | |
| 2010/0136144 A1 | 6/2010 | Msika | |
| 2015/0265527 A1 | 9/2015 | Su et al. | |
| 2016/0128367 A1 | 5/2016 | Huntsman | |
| 2017/0065654 A1 | 3/2017 | Rubin | |
| 2021/0137826 A1 | 5/2021 | Lin et al. | |

OTHER PUBLICATIONS

International Search Report and Written Opinion for PCT/US2024/032525, mailed Sep. 3, 2024, 11 pages.
Lifevantage Corporation. "Liquid Collagen" WEB. Downloaded from the URL: Https://cdn.lifevantage.com/wp-content/uploads/sites/2/2023/02/23153553/230216_02-AU-NZ-TS-Liquid-Collagen-Product-Info_Sheet.pdf. Mar. 14, 2023; <Entire Document>.
Pawar, et al. "Development of Regulatory Mechanism of Food Product Accessible Antioxidants: Lycopene and Curcumin" International Journal of Engineering and Advanced Technology vol. 9 Issue-1S3. Dec. 2019; <pp. 64-65, table 1>; <DOI: 10.35940/ijeat.A1013.1291S319>.
Chang H. C, Lin Y. K, Lin Y. H, Lin Y. H, Hu W. C, Chiang C. F. Hydrolyzed Collagen Combined with Djulis and Green Caviar Improve Skin Condition: A Randomized, Placebo-Controlled Trial. Curr Res Nutr Food Sci 2021; 9(2). doi : http://dx.doi.org/10.12944/CRNFSJ.9.2.16.
LifeVantage Corporation. (2022) Efficacy Evaluation of Red Quinoa.
Lin, P, Alexander, RA, Liang, C-H, et al. Collagen formula with Djulis for improvement of skin hydration, brightness, texture, crow's feet, and collagen content: A double-blind, randomized, placebo-controlled trial. J Cosmet Dermatol. 2021; 20: 188-194. https://doi.org/10.1111/jocd.13500.

* cited by examiner

*Primary Examiner* — Terry A Mckelvey

(74) *Attorney, Agent, or Firm* — Kenneth E. Horton; Barnes & Thornburg LLP

(57) ABSTRACT

Nutritional supplements and compositions for activating cellular signaling genes in innate inflammatory pathways are described in this application. In particular, this application describes a composition containing a solid portion comprising *Bacopa monnieri* extract having a least 20 percent bacosides, *Silybum marianum* (milk thistle) extract having 70 percent to about 80 percent silymarin, milk thistle extract, *Withania somnifera* (ashwagandha) extract, *Camellia sinensis* (green tea) extract containing at least 40 percent epigallocatechin gallate and about 98 percent polyphenols; and *Curcuma longa* (turmeric) extract containing at least about 95 percent curcumin. The compositions also comprise a liquid portion comprising fish collagen peptides comprising about 90 percent protein and *Formosa* ruby quinoa water extract containing about 10 wt % extract and about 90 wt % water. These compositions improved the skin and impacted key regulatory genes associated with several important cellular pathways. Other embodiments are also described.

21 Claims, 10 Drawing Sheets
Specification includes a Sequence Listing.

SEQUENCE LISTING

```
Sequence total quantity: 2
SEQ ID NO: 1           moltype = RNA   length = 58
FEATURE                Location/Qualifiers
source                 1..58
                       mol_type = other RNA
                       organism = synthetic construct
SEQUENCE: 1
agatcggaag agcgtcgtgt agggaaagag tgtagatctc ggtggtcgcc gtatcatt      58

SEQ ID NO: 2           moltype = RNA   length = 65
FEATURE                Location/Qualifiers
source                 1..65
                       mol_type = other RNA
                       organism = synthetic construct
SEQUENCE: 2
gatcggaaga gcacacgtct gaactccagt cacggatgac tatctcgtat gccgtcttct      60
gcttg                                                                 65
```

COMPOSITION AND METHODS FOR ACTIVATING CELLULAR SIGNALING GENES IN INNATE INFLAMMATORY PATHWAYS

REFERENCE TO SEQUENCE LISTING

The present application contains, as a separate part of the disclosure, a Sequence Listing in XML format. The file name is: 94344-388929 Sequence Listing.xml, created on Jun. 5, 2023, 2.7 KB, which is incorporated by reference herein, in its entirety.

BACKGROUND

This application relates to compositions for alleviating inflammation and oxidative stress in a subject. Specifically, this application describes nutritional supplements and compositions for activating cellular signaling genes in innate inflammatory pathways.

SUMMARY

This application relates generally to nutritional supplements and compositions for activating cellular signaling genes in innate inflammatory pathways. The compositions contain a solid portion comprising *Bacopa monnieri* extract having a least 20 percent bacosides, *Silybum marianum* (milk thistle) extract having 70 percent to about 80 percent silymarin, milk thistle extract, *Withania somnifera* (ashwagandha) extract, *Camellia sinensis* (green tea) extract containing at least 40 percent epigallocatechin gallate and about 98 percent polyphenols; and *Curcuma longa* (turmeric) extract containing at least about 95 percent curcumin. The compositions also comprise a liquid portions comprising fish collagen peptides comprising about 90 percent protein and *Formosa* ruby quinoa water extract containing about 10 wt % extract and about 90 wt % water. These compositions improved the skin and impacted key regulatory genes associated with several important cellular pathways.

BRIEF DESCRIPTION OF DRAWINGS

The following description can be better understood in light of the Figures which show various embodiments and configurations of the imaging systems and methods. Together with the following description, the Figures demonstrate and explain the structures, methods, and principles described herein. In the drawings, the thickness and size of components may be exaggerated or otherwise modified for clarity. The same reference numerals in different drawings represent the same element, and thus their descriptions will not be repeated. Furthermore, well-known structures, materials, or operations are not shown or described in detail to avoid obscuring aspects of the described devices.

DETAILED DESCRIPTION

Figure 1A:
FIGS. 1A-D illustrate improvements in the skin of individuals ingesting some formulations of the compositions described herein.

The following description supplies specific details in order to provide a thorough understanding. Nevertheless, the skilled artisan will understand that the described X-ray systems can be implemented and used without employing these specific details. Indeed, the described systems and methods can be placed into practice by modifying the described systems and methods and can be used in conjunction with any other apparatus and/or techniques conventionally used in the industry. For example, while the description below focuses on nutritional supplements and cosmetics for humans, it could be adapted and modified for other industries such as animals or other uses such as being part of a functional food.

The National Institute of Health defines aging as a "complex process that results from a combination of environmental, genetic, and epigenetic factors." A chronic pro-inflammatory status is a pervasive feature of aging. This chronical, low-grade inflammation is known as "inflammaging" and contributes to the pathogenesis of age-related diseases such as autoimmune diseases like rheumatoid arthritis; cardiovascular diseases like high blood pressure and heart disease; gastrointestinal diseases like inflammatory bowel disease; lung diseases such as asthma; mental illnesses such as depression; metabolic diseases such as Type 2 Diabetes; neurodegenerative diseases such as Parkinson's disease; skin diseases such as acne and dermatitis; as well as some types of cancers such as colon cancer. Inflammaging is the long-term result of the chronic physiological stimulation of the innate immune system, which can become damaged during aging.

The immune system is typically divided into two arms, the innate and adaptive systems. The innate immune system serves to control most pathogens in a more rapid, less energy expending manner than the adaptive immune system, and to help regulate subsequent immune responses, guiding and controlling them in order to most efficiently clear pathogens with a minimum of pathological side effects. So the adaptive immune system is carefully regulated so as to be activated only when necessary. Among the first elements of the innate system that pathogens encounter are pattern recognition receptors, invariant receptors that detect conserved pathogen associated molecular patterns. Upon recognizing its binding ligand, a pattern recognition receptor will activate a signaling cascade that often triggers production and/or release of one or more pro-inflammatory cytokines. These in turn modulate additional elements of both the innate and adaptive immune responses, and are often critical lynchpins of host defense.

In some embodiments, the compositions described herein contain a solid portion and a liquid portion that can be combined to modulate this inflammaging process to minimize age-related damage of the bodily systems through overstimulation of the innate immune system. The compositions described herein contain a solid portion (or part) and a liquid portion (or part) that can be combined to achieve this function. The solid and liquid portions can be kept separate and administered at substantially the same time or can be mixed together and then administered to an individual. In some formulations, the compositions contain about 162.5 mg to about 2700 mg of the solid portion and about 12.5 ml to about 100 ml of the liquid portion. In other formulations, the compositions contain about 325 mg to about 1350 mg of the solid portion and about 25 ml to about 75 ml of the liquid portion. In yet other formulations, the compositions contain about 675 mg of the solid portion and about 50 ml of the liquid portion. The compositions can also contain any combination or range of these amounts.

The solid portion contains a mixture containing at least two of the following nine plant derived active agents, which are listed in the Table 1 along with the desired amounts of each agent. In one aspect, an antioxidant-inducing agent further comprises any of the following nine plant derived active agents, which are incorporated into the antioxidant-inducing preparation in currently preferred concentrations (wt/wt) ranging from about 0.001 mg to about 1000 g, preferably about 0.1 mg to about 10 g, more preferably about 1 mg to about 2 grams, and most preferably about 50 mg to about 500 mg.

TABLE 1

| ACTIVE AGENT | AMOUNT (Per dosage Unit) |
|---|---|
| *Bacopa monnieri* extract | 0.001 mg to 1000 g |
| Gotu Kola powder | 0.001 mg to 1000 g |
| Ashwagandha powder | 0.001 mg to 1000 g |
| Green tea 98% (Polyphenols 45% EGCG) | 0.001 mg to 1000 g |
| Turmeric extract 95% | 0.001 mg to 1000 g |
| Milk Thistle extract 70-80% | 0.001 mg to 1000 g |
| *Aloe vera* powder | 0.001 mg to 1000 g |
| *Ginko Biloba* leaf extract | 0.001 mg to 1000 g |
| N-Acetyl Cysteine | 0.001 mg to 1000 g |

Details about these nine active ingredients are described in U.S. Pat. No. 8,435,574 ("the '574 Patent"), the entire disclosure of which is incorporated herein by reference.

By using a combination of some or all of these nine active agents in the respective amounts as listed in Table 2 to formulate a composition (e.g., an oral dietary supplement), the desirable effects are additive and even synergistic. The overall effect, then, is to upregulate at least one antioxidant enzyme (e.g., SOD, CAT, and GPX) while decreasing the concentration of free radicals and ROS and the rate of lipid peroxidation and other undesirable chemical reactions that result in oxidative stress on the body. For example, tissue level of thiobarbituric acid reactive chemical species (e.g., plasma TBARS) are reduced after administration of a composition of the invention to a subject. Furthermore, the likelihood of observing the undesired side effects listed for each respective active agent is more remote as each extract is diluted out by a factor of up to nine (9).

TABLE 2

| ACTIVE AGENTS | DOSAGE/DAY |
|---|---|
| *Bacopa monnieri* extract | 10-4,000 mg |
| Milk Thistle extract 70-80% | 15-6,000 mg |
| Ashwagandha powder | 10-4,000 mg |
| Turmeric extract 95% | 5-2,000 mg |
| Gotu Kola powder | 10-4,000 mg |
| *Aloe vera* powder | 10-4,000 mg |

TABLE 2-continued

| ACTIVE AGENTS | DOSAGE/DAY |
|---|---|
| Green tea, 98% Polyphenols 45% EGCG | 5-2,000 mg |
| *Ginko biloba* leaf extract | 5-2,000 mg |
| N-Acetyl Cysteine | 50-5,000 mg |

It is expected that the above-described active agents, in the amounts listed, will provide a combined remedy for oxidative stress that may be processed, in one embodiment, into a dosage unit for oral administration. This dosage unit is then administered, as a tablet, capsule, gel cap, pellet (globule), or in other carrier suitable for oral administration. Alternatively, the composition could be made available as a powder to be mixed with a suitable liquid, such as water, to form a tonic. In one embodiment, the formulation of the herb-containing composition of the invention is an oral dietary supplement. As such, an efficient, proper, and effective balance of these active agents can be formulated as to provide a composition that can be administered as a suitable daily oral dietary supplement.

In some embodiments, the composition(s) described herein contains at least two (2) of the components (e.g., ingredients) summarized in Table 2. In some embodiments, the herb-containing composition of the invention contains two (2), three (3), four (4), five (5), six (6), seven (7), eight (8), or nine (9) of the components summarized in Table 2. The herb-containing composition of the invention can contain the components summarized in Table 2 in any quantity, or combination, suitable to give the desired oxidant preventative, therapeutic, or alleviating effect.

The compositions can be used as a method of preventing, alleviating or treating oxidative stress in an individual. The active agents are formulated into a composition that retains the prophylactic and therapeutic antioxidant-inducing properties of the individual active agents, providing an additive or even synergistic antioxidant-inducing effect relative to the effect of each active agent alone, while also decreasing the toxic side effect(s) to a subject, of the individual active agents of the compositions. The compositions of the invention are useful to eradicate free and bound radical reactions presently taking place or may be used as prophylaxis against pathological free or bound radical reactions, which may occur as a result of a possible oxidant promoting incident (e.g., ischemic injury).

As described in the '574 Patent, the compositions can be used for increasing the levels of antioxidants via alteration of the activity level of SOD, CAT, and GPX enzymes in the body. The composition provides in one embodiment a mixture of herbal extracts of *Bacopa monnieri* (*B. monnieri* or *Bacopa*), which contains a high percentage of the active chemicals bacosides A & B. Ingestion of *Bacopa* induces SOD, CAT, and GPX and provides the beneficial activities thereof, with pronounced results in the brain. Studies have indicated that the bacosides also increase protein and serotonin levels while decreasing norepinephrine concentration in the hippocampus, hypothalamus, and cerebral cortex. *Bacopa* thus reduces the neurodegeneration in the brain that is caused by oxidative stress related to the accumulation of neurotoxic free radicals in the brain. Accordingly, it may be used to alleviate symptoms of neurodegenerative disorders such as memory loss, Alzheimer's disease, and Parkinson's disease, and even aging.

In some embodiments, the solid portion comprises a formulation with the following active ingredients: about 225 mg milk thistle (seed) extract with 80% silymarin; about 150 mg ashwagandha (root) extract with 0.35% withaferin A; about 75 mg green tea (leaf) extract with 45% EGCG; about 150 mg *Bacopa* (whole herb) extract with 45% bacosides; and about 75 mg turmeric (rhizome) extract with 95% curcuminoids, along with various binders, excipients, and flow agents. In other embodiments, the solid portion comprises a formulation with the following active ingredients: about 21 wt % milk thistle (seed) extract with 80% silymarin; about 13.4 wt % ashwagandha (root) extract with 0.35% withaferin A; about 6.7 wt % green tea (leaf) extract with 45% EGCG; about 13.4 wt % *Bacopa* (whole herb) extract with 45% bacosides; and about 6.7 wt % turmeric (rhizome) extract with 95% curcuminoids, along with various binders, excipients, and flow agents.

In other embodiments, the solid portion comprises the formulations described in Tables 3, 5, 7, and/or 8 of the '574 Patent. When administered to an individual as described in the '574 Patent, they have any or all of the beneficial effects described in that patent.

The liquid portion of the composition contains two or more active ingredients. One of those active ingredients is fish collagen peptides. The other active ingredient is *Formosa* ruby quinoa. Another active ingredient that could be included includes food sources that contain lycopene, such as tomatoes, pink grapefruit, watermelon, papaya, guava, sweet red pepper, persimmon, asparagus, red cabbage, mango, and combinations thereof. Other active ingredients that could be used in the liquid portion are an herbal combination of blueberry/young ponkan citrus extract, a combination of black tea and citrus, a combination of black tea and spinach, a combination of green tea and citrus, a combination of green tea and spinach, a combination of citrus and oolong tea, a combination of spinach and pu'er tea, a combination of green coffee bean and blueberry, a combination of green coffee bean and pu'er tea, a combination of red wine extract and blueberry, a combination of spinach and blueberry, and combinations thereof. In some embodiments, the herbal combination comprises a combination of young ponkan fruit and blueberry powder. In some formulations, these ingredients can serve both as an active ingredients and a flavoring (described below).

The fish collagen peptide is a type of collagen protein. Collagen is the most abundant protein in the body and is made of amino acids. Its fiber-like structure is used to make connective tissue and therefore is a major component of skin, bone, muscles, tendons, ligaments, and cartilage, helping to make tissues strong and resilient. Collagen is also present in the skin, allowing for the elasticity needed to be stretched and then returned back to normal.

Collagen cannot be absorbed into the body in its whole form; therefore, it needs to be broken down into smaller particles called peptides. A peptide is a short chain of amino acids that are linked together by chemical (peptide) bonds. Collagen peptides are made by extracting collagen from animals such as cows, fish, and chickens, as well as other sources. Once extracted, the collagen is put through a process called hydrolysis, which heats and breaks down the collagen in order to maximize ease of absorption by the body. This broken-down form of collagen, now called collagen peptides or hydrolyzed collagen, can be absorbed through the gastrointestinal tract.

Fish collagen peptides are produced from the skins of fish. They are type I collagen peptides which are the building blocks for beautiful skin, flexible connective tissues and strong bones. The production process behind fish collagen peptides is the same as it is for collagen peptides from any other source. It begins with a natural process of extracting gelatin from the raw material, which contains native collagen. This is followed by a specific enzymatic hydrolysis process to convert the gelatin into—highly bioavailable and bioactive—collagen peptides.

The amount of fish collagen peptides in the liquid portion of the composition can be any amount that provides the desired peptide concentration. In some embodiments, the liquid portion contains about 500 mg to about 15,000 mg of fish collagen peptides. In other embodiments, the liquid portion contains about 1000 mg to about 10,000 mg of fish collagen peptides. In yet other embodiments, the liquid portion contains about 5000 mg of fish collagen peptides containing about 90 percent protein. The liquid portion can contain any range or combination of these amounts of fish collagen peptides.

In some embodiments, the liquid portion contains about 1 wt % to about 30 wt % of fish collagen peptides. In other embodiments, the liquid portion contains about 2 wt % to about 20 wt % of fish collagen peptides. In yet other embodiments, the liquid portion contains about 10 wt % of fish collagen peptides containing about 90 percent protein. The liquid portion can contain any range or combination of these amounts of fish collagen peptides.

The second active ingredient in the liquid portion is *Formosa* ruby quinoa (or red quinoa) extract. Also known by the name *Chenopodium formosanum (djulis)*, it is a close relative of quinoa and belongs to the Chenopodiaceae family and the genus *Chenopodium*. It contains a high content of essential amino acids and flavonoids. The *Formosa* ruby quinoa is extracted from its natural source by reverse osmosis (RO) filtration so that the extract contains about 10 wt % of the extract and about 90% water. Additional details and information about the *Formosa* ruby quinoa ingredient are described in U.S. Publication No. 2021/0137826, the disclosure of which is incorporated herein by reference.

The amount of red quinoa extract in the liquid portion of the composition can be any amount that provides the desired amount of vitamins and/or minerals. In some embodiments, the liquid portion contains about 500 mg to about 10,000 mg of the red quinoa extract. In other embodiments, the liquid portion contains about 1000 mg to about 10,000 mg of the red quinoa extract. In yet other embodiments, the liquid portion contains about 5000 mg of red quinoa extract containing about 10 percent extract and about 90 wt % water. The liquid portion can contain any range or combination of these amounts of the red quinoa extract.

In some embodiments, the liquid portion contains about 1 wt % to about 30 wt % of the red quinoa extract. In other embodiments, the liquid portion contains about 2 wt % to about 20 wt % of the red quinoa extract. In yet other embodiments, the liquid portion contains about 10 wt % of the fish collagen peptides containing about 10 percent extract and 90 wt % water. The liquid portion can contain any range or combination of these amounts of the red quinoa extract.

The amount of the lycopene-containing food source in the liquid portion of the composition can be any amount that provides the desired amount of lycopene. In some embodiments, the liquid portion contains about 500 mg to about 10,000 mg of the lycopene-containing food source. In other embodiments, the liquid portion contains about 1000 mg to about 10,000 mg of the lycopene-containing food source. In yet other embodiments, the liquid portion can contain any range or combination of these amounts of the lycopene-containing food source.

In some embodiments, the liquid portion contains about 1 wt % to about 30 wt % of the lycopene-containing food source. In other embodiments, the liquid portion contains about 2 wt % to about 20 wt % of the lycopene-containing food source. The liquid portion can also contain any range or combination of these amounts of the lycopene-containing food source.

The amount of the herbal combination in the liquid portion of the composition can be any amount that provides the desired amount of vitamins and/or minerals. In some embodiments, the liquid portion contains about 50 mg to about 1000 mg of the herbal combination. In other embodiments, the liquid portion contains about 100 mg to about 500 mg of the herbal combination. In yet other embodiments, the liquid portion contains about 150 mg of the herbal combination. In even other embodiments, the liquid portion can contain any range or combination of these amounts of the herbal combination.

In some embodiments, the liquid portion contains up about 1 wt % of the herbal combination. In other embodiments, the liquid portion contains about 0.1 wt % to about 0.5 wt % of the herbal combination. In yet other embodiments, the liquid portion contains about 0.3 wt % of the herbal combination. In even other embodiments, the liquid portion can contain any range or combination of these amounts of the herbal combination.

The liquid portion can also contain flavorings, preservatives, solvents, buffers, emulsifiers, suspending agents, decomposers, disintegrating agents, dispersing agents, binding agents, excipients, stabilizers, chelating agents, diluents, gelling agents, wetting agents, lubricants, absorption delaying agents, liquids, and combinations thereof. In some embodiments, the liquid portion contains flavorings and/or preservatives.

The flavorings that can be used in the liquid portion include apple juice concentrate, cranberry-raspberry flavorings, strawberry flavorings, blueberry powder, young ponkan fruit extract, acerola berry extract, citric acid, the flavorings that also serve as active ingredient as described above, and combinations thereof. In some embodiments, the flavorings include apple juice concentrate, cranberry-raspberry flavorings, strawberry flavorings, blueberry powder, young ponkan fruit extract, acerola berry extract, and citric acid. In some embodiments, the liquid portion contains about 20 wt % to about 30 wt % flavorings. In other embodiments, the liquid portion contains about 25 wt % flavorings.

The preservatives that can be used in the liquid portion include potassium sorbate, e-polylysine, sormate, rosemary extract, sodium benzoate, citrus extract, glycerin, fructooligosaccharid, berry extract and tapioca starch, cultured sugar cane, and any combinations thereof. In some embodiments, the preservatives that can be used in the liquid portion include potassium sorbate. In other embodiments, the liquid portion contains about up to about 0.1 wt % preservatives. In yet other embodiments, the liquid portion contains about 0.05 wt % preservatives.

The remainder of the liquid portion of the composition comprises a liquid. The liquids that can be used include fruit juices and/or water. In some embodiments, water is used as the liquid. In some embodiments, the liquid portion contains about 50 wt % to about 60 wt % water. In other embodiments, the liquid portion contains about 55 wt % water.

In some formulations, the liquid portion comprises the following three ingredients: (i) about 5000 mg fish collagen peptides with 90 percent protein; (ii) about 5000 mg *Formosa* ruby quinoa extract (*Chenopodium formosanum*) with 10% (or 500 mg) extract and 90% (or 4500 mg) water; and (iii) about 27,825 gm water, along with various flavorings and preservatives. In other formulations, the liquid portion comprises the following three ingredients: (i) about 10 wt % fish collagen peptides with 90 percent protein; (ii) about 10 wt % *Formosa* ruby quinoa extract (*Chenopodium formosanum*) with 10 percent extract and 90 percent water; and (iii) about 55.5 wt % water, with the remainder being various flavorings and preservatives.

The liquid portion can be made by any methods that will arrive at the desired concentration of ingredients. These methods include blending processes, homogenizing all ingredients at the same time, and/or any mixing processes.

These ingredients in the solid and liquid portions can be combined to prepare an antioxidant composition, a composition that improves the expression of antioxidant-related genes (such as the SOD1 gene, the SOD2 gene, or the CAT gene) in cells, a composition for enhancing antioxidant enzymes in the body, a skin moisturizing composition, a composition that improves the expression of moisturizing-related genes (such as the TGM1 gene, the KRT1 gene, the KRT10 gene, the KRT14 gene) in cells, a skin whitening composition, a composition that inhibits tyrosine expression, a composition that inhibits melanin formation, or a wrinkle soothing and/or skin texture improving composition.

In some embodiments, the composition can be manufactured into a medicament or formula suitable for non-parenteral or oral administration. These medicaments or formulas may include tablets, troches, lozenges, pills, capsules, dispersible powders, granules, solutions, suspensions, emulsions, syrups, elixirs, slurries, injections, sterile powders, external preparations (external preparation), and/or other medicaments or formulas having similar functions.

In some embodiments, the composition may be a food composition such as a food product or a food additive. The food additive refers to a matter that is added to manufacture a food product with conventional methods or is added during the production process of a food product. This food product can be formulated with edible materials, and the food product can be consumed by humans or animals. The food product may be but is not limited to: drinks (beverages), fermented foods, bakery products, health foods, dietary supplements, and/or nutritional supplements.

In some embodiments, the combination of the ingredients from the two portions influenced the appearance of fine lines and wrinkles, skin elasticity, skin tone and skin texture. It also influenced skin moisture, skin collagen density, and skin tone evenness. These observations were captured in before-and-after photos captured by the users of the composition. Based on the positive physical results observed from the combination, the mechanisms of action using RNA sequencing techniques were investigated. The combination of the ingredients from the two portions surprisingly showed a synergistic impact on key regulatory genes associated with several important pathways such as the innate immune system, which deals directly with inflammatory responses to a disease or other insult to the body, and metabolism pathways such as glucose metabolism, energy metabolism, and structural cell integrity pathways. In addition, the pathways relating to male fertility development, stress responses and DNA transcription/replication processes were also positively impacted. Activation of the genes involved in these pathways and processes addresses the signaling pathways that are involved in inflammation and the resulting diseases/issues.

Example: Anti-Oxidation and Skin Condition Improvement

A clinical study was carried out on individuals to test the effect of the compositions described herein. A total of 80-100 healthy individuals aged >30 years old volunteered in this study. The subjects were already taking Protandim Nrf2 Synergizer® at the time they entered the study. Subjects were then instructed to switch to a regimen of consuming a composition with a liquid portion (containing 5 g of a red quinoa mixture containing 500 mg red quinoa extract and 4500 mg water and 5 g of fish collagen power, along with some flavorings) together with the active ingredients of the solid portion (containing 225 mg Milk Thistle extract, 150 mg Ashwagandha extract, 150 mg *Bacopa monnieri* extract, 75 mg Green tea extract, and 75 mg Turmeric extract) every day for at least 30 days. Subjects were asked to take pictures at day 0 before the start of consuming this composition with the liquid portion and the solid portion to get a baseline reference point, as well any day up to day 30 and any other day thereafter if they chose to continue in the study. Some subjects stayed in the study longer than 30 days, even up to 7 months. Pictures were taken using the subject's own photographic device, in the same spot, and at the same time of each day.

Subjective evaluation of the day 0 and periodic day pictures were made, paying attention to the following criteria: fine lines and wrinkles, pigmentation of the skin evaluated, skin tone, skin firmness, and skin evenness. Surprising results were visible to the naked eye. After long-term use of this composition, a distinct improvement in the appearance of fine lines and wrinkles in the face were seen in all subjects, as well as improvement in pigmentation blemishes.

Figure 1B:
Figure 1C:
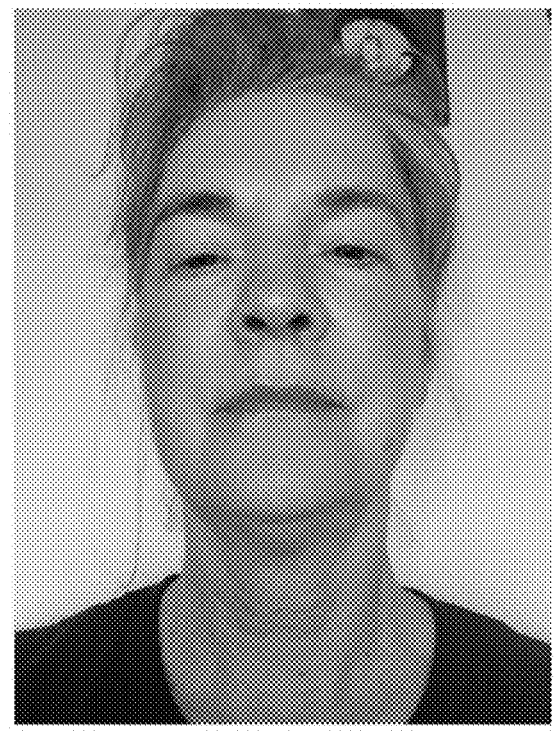
Figure 1C:
Figure 1D:
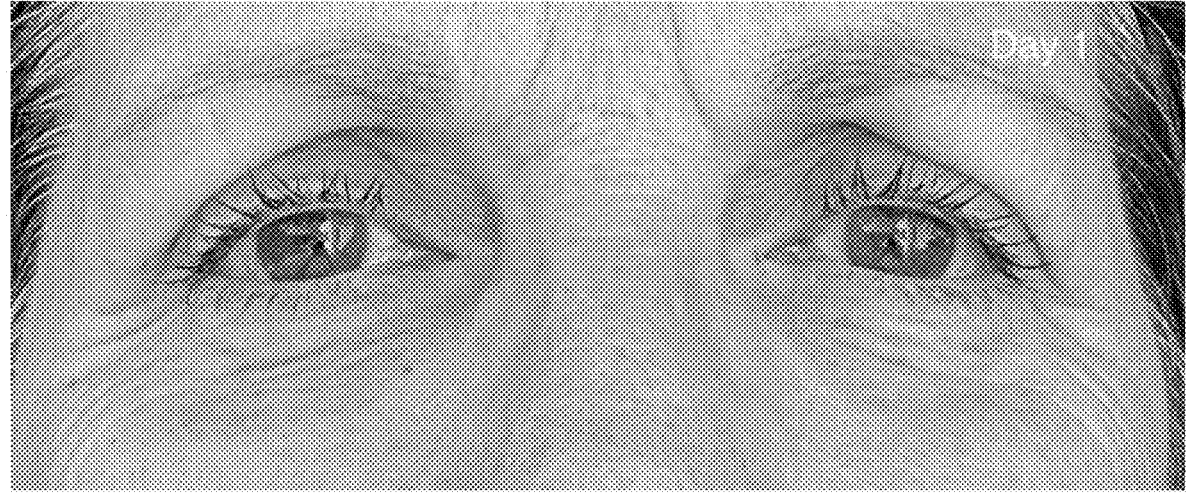
Figure 1D:
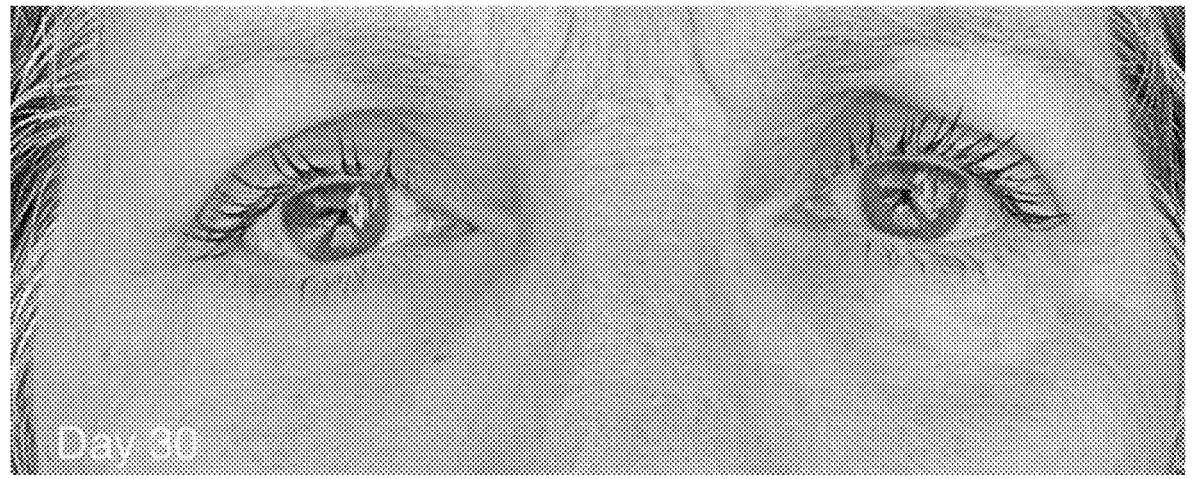

As an example of these results, the following photographic results were obtained by the subjects. FIG. 1A depicts before-and-after photographs of a subject after 15 days of using both portions of the composition. The appearance of the under-the-eye circles has been diminished, showing improved collagen density and blood circulation under the eyes. FIG. 1B shows before-and-after photographs of a subject after 20 days of using both portions of the composition. The appearance of deep lines and wrinkles, especially around the eye area, has been diminished over the entirety of the face and the skin tone has evened out. FIG. 1C depicts before (left) and after (right) photographs of a subject after 30 days of using both portions of the composition. The appearance of deep lines and wrinkles has been diminished over the entirety of the face, including down to the neck. FIG. 1D shows before-and-after photographs of the same individual after 30 days of using both portions of the composition. The appearance of deep lines and wrinkles has been diminished around the eyes.

Based on these positive photographic results, RNA sequencing was performed on the solid portion of the composition, the liquid portion, as well as on the combination of both portions in a fibroblast cell culture. RNA sequencing was used for detection and quantitative analysis of messenger RNA molecules in a biological sample and for studying cellular responses.

The RNA sequencing was performed by seeding CCD-986Sk normal human fibroblasts into 10 cm dishes and allowed to attach overnight. Cells were then treated at 75% confluency with 50 μL of test article (0.5% DMSO final concentration). Cells were lysed and RNA was isolated at the 8 hour specified time point (Zymo Quick RNA MiniPrep system). RNA QC, library construction, library QC, sequencing, and trimming were performed by Novogene (Sacramento, CA) as follows.

RNA samples were evaluated for RNA integrity using an Agilent 2100 Bioanalyzer.

Messenger RNA was purified from total RNA using poly-T oligo-attached magnetic beads. After fragmentation, the first strand cDNA was synthesized using random hexamer primers followed by the second strand cDNA synthesis. The library was ready after end repair, A-tailing, adapter ligation, size selection, amplification, and purification. Following is the workflow of library construction: mRNA>Fragmentation>Reverse transcription>Second strand cDNA synthesis >End repair and A-tailing>Adapter ligation>Size selection>PCR amplification. The library was checked with Qubit and real-time PCR for quantification and bioanalyzer for size distribution detection. All samples passed quality control.

Samples were sequenced on an Illumina NovaSeq instrument for paired end 150 bp reads. 40-50 million reads were obtained for each sample. All resulting sequencing reads were filtered by removing adapters, removing reads containing N>10% (N represents a base that cannot be determined), and removing reads containing low quality (Qscore≤5) bases (removed when low quality bases represent over 50% of the total bases).

(SEQ ID NO: 1)
5' Adapter:
5'AGATCGGAAGAGCGTCGTGTAGGGAAAGAGTGTAGATCTCGGTGGTCG
CCGTATCATT-3'.

(SEQ ID NO: 2)
3' Adapter:
5'GATCGGAAGAGCACACGTCTGAACTCCAGTCACGGATGACTATCTCGT
ATGCCGTCTTCTGCTTG-3'.

The RNA sequencing was performed by seeding CCD-986Sk normal human fibroblasts into 10 cm. All samples had approximately 97% of reads being clean reads that passed filtering. FASTQ read files from the filtered sequencing were processed using Galaxy (useGalaxy.org). FASTQ files were aligned with HISAT2 (Galaxy Version 2.2.1) using human b38 hg38 canonical female (cell line was female). HISAT2 was performed with "Unstranded" and "Paired end" options selected. The resulting SAM file produced with HISAT2 was used to generate count tables for each sample using the program FeatureCounts (Galaxy Version 2.0.3). Count tables were then input into Limma Voom to perform differential gene expression (relative to DMSO control) (Limma, Galaxy Version 3.50.1). Limma settings included gene filtration set to require at least 2 samples having at least 1 count per million. Differential expression was ranked by adjusted P-value and gene enrichment analysis was performed (rank ordered by NES value (Normalized Enrichment Score)). The gene sets C2 and C5 from https://www.gsea-msigdb.org/gsea/msigdb/human/collections.jsp#C2 were then used in the analysis.

A total of 13,708 genes were influenced, which were distributed over 18,671 cellular pathways. Of those 13,708 genes, 18% (or 2466 genes) showed significant up or down regulation either by the liquid portion, the solid portion, or the combined portions. Neither the liquid portion nor the solid portion alone significantly affected gene expression. For the 2466 genes that were regulated, the combination of both portions influenced 2412 genes (p<0.05) of which 418 genes (17.3%) were significantly up regulated (195 genes) or down regulated (223 genes). For these 418 genes, 80 genes showed a change compared to the solid portion alone between in the following categories, as illustrated in the tables below.

Figure 2A:
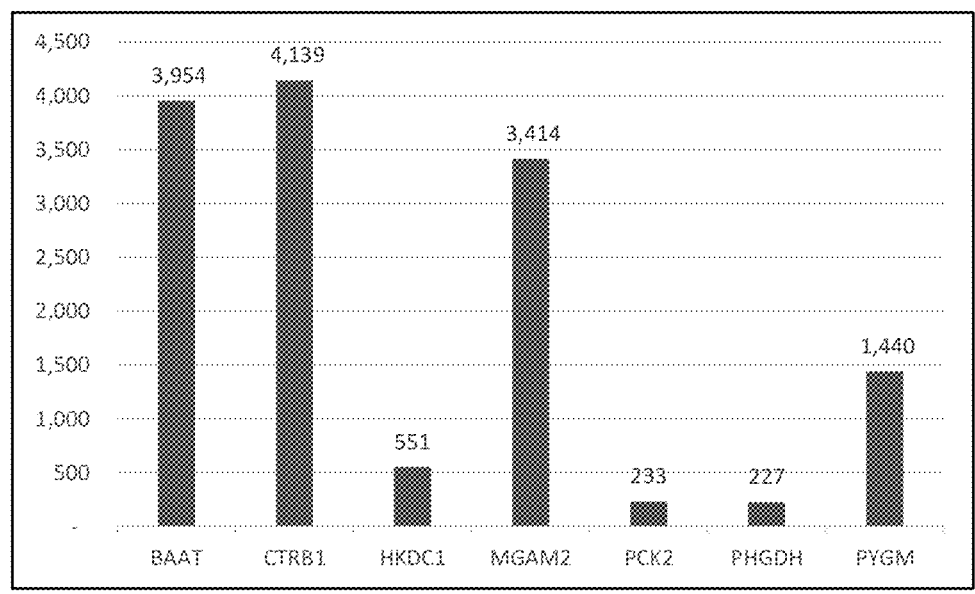
FIGS. 2A-D show the impact on the metabolism of individuals ingesting some formulations of the compositions described herein.

FIG. 2A shows the impact of the combined portions of the composition on the metabolism. FIG. 2A shows increase in mRNA gene activation for proteins that catalyze reactions as compared to the liquid portion alone. This increase in mRNA gene expression for proteins is involved in metabo- lizing carbohydrates (MGAM2), such as glucose (HKDC1, PYGM), fats such as cholesterol (BAAT), proteins (CTRB1), and amino acids (PCK2, PHGDH). The increased mRNA gene activation allows for improved metabolism of macronutrients to be utilized in energy production and cell turn-over. Macronutrients for humans are classified as car- bohydrates, protein, and fats. They are needed in larger amounts as compared to micronutrients, which are the vitamins and minerals. Carbohydrates fuel the body by being broken down into glucose. Glucose then enters the bloodstream and can become an immediate source of energy or be stored in specialized cells for later use. Proteins are broken down into amino acids which are specialized build- ing blocks for various structures in the body such as muscles, brain, skin, blood vessels, and nervous system. Amino acids are further used to create smaller proteins that act as signaling and communication molecules between cells and also act inside each cell. These communication mol- ecules become important for the function of cellular pro- cesses. Fats, also called lipids or fatty acids, provide an important source for energy production under calorie restric- tion/starvation. However, lipids are also essential for proper cell functions where they also act as signaling molecules and support cell membranes and can also become part of hor- mone structures.

Figure 2B:
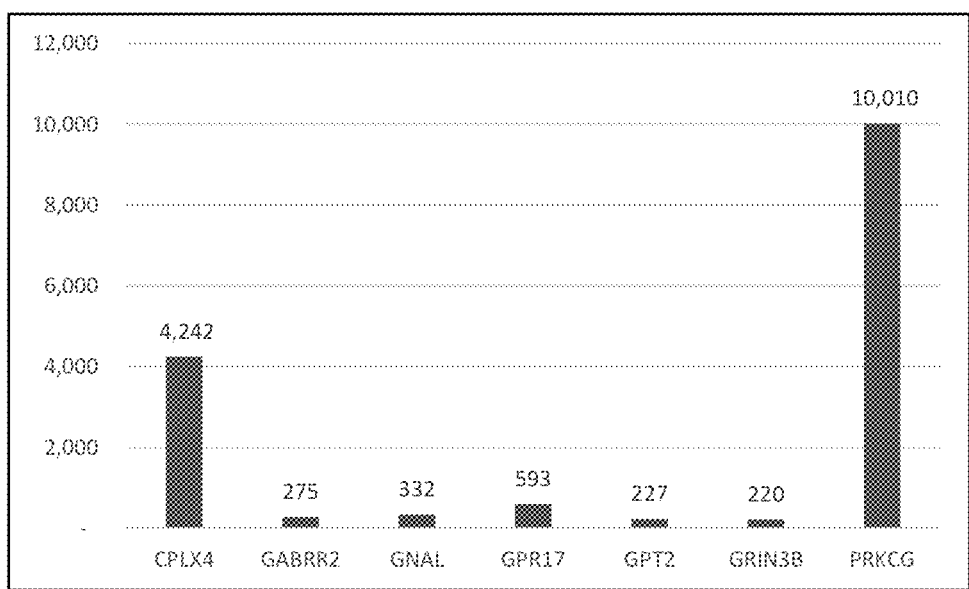

FIG. 2B also shows the impact of the composition on the metabolism. This figure shows the increase in mRNA gene activation for proteins involved in nerve cell communica- tions as compared to the liquid portion alone. FIG. 2B shows the change in mRNA gene expression for proteins involved in neuronal health (GPR17, GPT2), nerve cell signaling for information processing between neuronal cells (GABRR2, PRKCG), and neuronal metabolism (CPLX4, GNAL, GRINB3). All of these genes are upregulated, suggesting that cell signaling between the neuronal cells are more efficient and the information exchanged is processed quicker. Nerve cells, also called neurons or neuronal cells, are important players in activating the nervous system. Within the neurons, information is transported through elec- trical impulses, and between neurons chemical reactions are used to relay information from neuron to neuron. Neurons are different cells than the normal cell in the rest of the body. Neurons have three parts: the cell body, tendrils, and axon. The cell body carries out most of the basic cellular functions for metabolism and upkeep. The tendrils are thin fibers that extend from the cell body in a branched way to obtain and receive information from other neurons. The axon is a long thin fiber that carries nerve impulses to other neurons. The nerve signals often travel long distances and are crucial in relaying information to and from the point of where it is received. Within the neuron, neurotransmitters, which are small chemical messenger molecules, are created and secreted to affect or talk to another neuron via receptors on their cell surface. The efficiency and the speed of these reactions determines the interpretation and the outcome of the information processed. These neurotransmitters are help- ful to the proper functioning of the brain and other nervous systems.

Figure 2C:
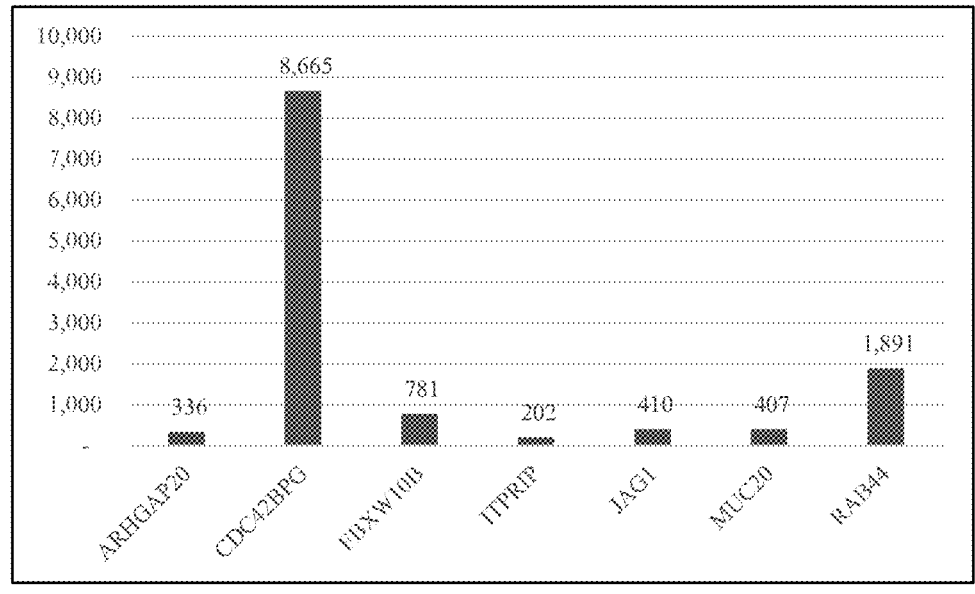

FIG. 2C shows the impact of the composition on the metabolism. This figure shows changes in mRNA gene activation for proteins involved in several cell signaling pathways as compared to the liquid portion alone, including the change in mRNA expression for proteins involved in cell signaling activities/regulation (AEHGAP20, ITPRIP, JAG1, MUC20, RAB44) and protein configuration changes/activa- tion (CDC42BBPG, FBXW10B). All of these genes are upregulated, suggesting better communication between the cells through activating cell signaling proteins. Biological systems use cell signaling or cell communication to talk to other cells or within the cell to receive, process, and transmit signals (answer) to its environment. Small proteins, lipids, amino acids, or combinations thereof are usually signaling molecules, but in order for them to be activated they have to have a chemical or conformational (physical) change. Cell signaling is a fundamental part of life and the more effi- ciently these communication signals occur, the healthier the human body will be.

Figure 2D:
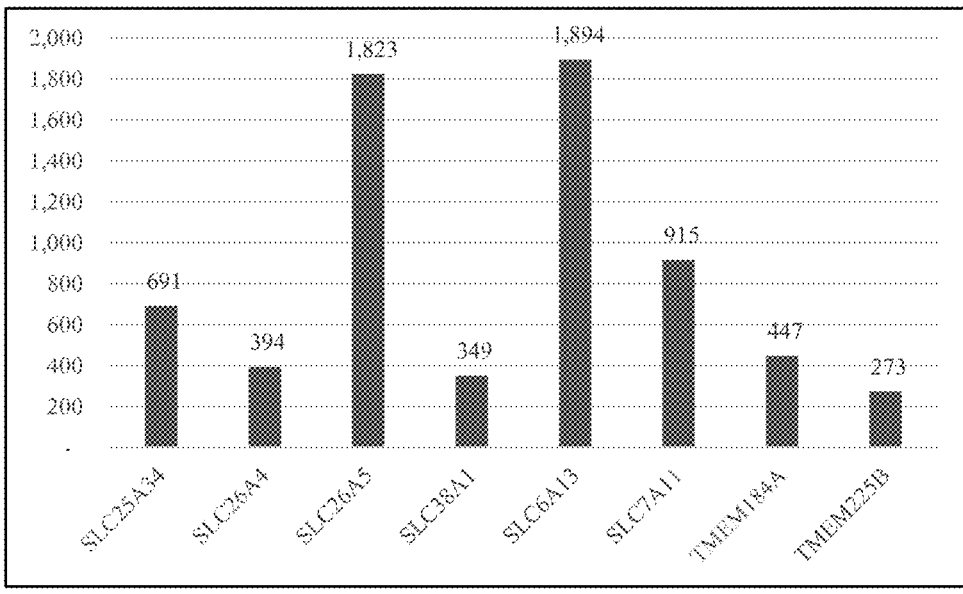

FIG. 2D also shows the impact of the composition on the metabolism. This figure shows an increase in mRNA gene activation for transporter proteins found in membranes throughout cells as compared to the liquid portion alone, including the change in mRNA gene expression for transport proteins found in mitochondrial (SLC25A34) and outer cell membranes (SLC26A4, SLC26A5, SLC38A1, TMEM184A, TMEM225B) and ion/cation transport chan- nels (SLC6A13, SLC7A11). All the genes are upregulated, suggesting that both the mitochondrial and outer cell mem- branes allow a more efficient transport across the mem- branes of required proteins and minerals. Transport proteins are small molecules that transport other types of materials within an organism. They are essential for growth and survival of organisms. There are various transport proteins depending on their roles. Some are associated with the outer cell membrane while others are located in the nuclear cell membrane or mitochondrial cell membranes. As their name suggests, these specialized proteins help or facilitate the movement of other molecules and they are each created for a specific function. Some of these molecules that need to be transported across the membranes are sodium and chloride ions, glucose molecules, amino acids, retinols and other non-polar molecules. Some of these molecules when trans- ported across the membrane have a conformational or chemical change that makes them active or inactive.

Figure 3A:
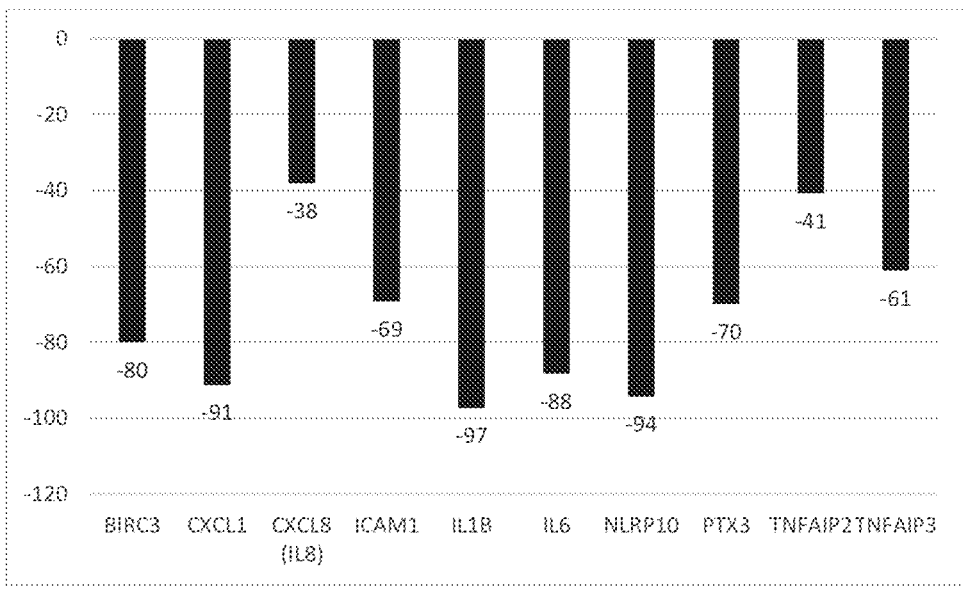
FIGS. 3A-C show the impact on the innate immune system of individuals ingesting some formulations of the compositions described herein.

FIG. 3A shows the impact of the combined portions of the composition on the innate immune system. The innate immune system plays an important role in the immediate response to any insult from a tissue injury to a pathogen invasion. Inflammation is the primary response and is stimu- lated by chemical changes in injured cells. The immediate inflammatory response is redness to the skin, heat with or without swelling, pain, and possible dysfunction of the organ involved. One of the rapid-acting primary transcrip- tion factor and key regulator of the inflammatory pathway or cascade is the Nuclear Factor kappa B Complex (NF-kB). This complex is composed of several proteins together (REL, NFKB, NFKA, IKK) and can be found as a deacti- vated complex or an activated complex. Upon activation, the NF-kB complex allows the reactions to process and results in the production of small signaling proteins called cytok- ines. Cytokines are important in our immune system because they balance the immune response. Some cytokines cause inflammatory reactions, such as interleukin-1, -6, and -8, and are often called pro-inflammatory cytokines. Complex bio- chemical reactions occur for this response, which also involves helper proteins that allow cells to stick to each other, proliferate, and cause further destruction. Excessive chronic inflammation can lead to inflammatory diseases such as atherosclerosis, arthritis, premature aging, and can- cer. A healthy balance of pro-inflammatory and anti-inflammatory cytokines is desirable, and the body has an associated regulatory system. There are also proteins that interfere with the assembly of the NF-kB complex (NFKBIB) by complexing with it, thus trapping it in the cell. There are also proteins that will modulate (TRIB3) the inflammatory pathways and act as anti-inflammatory agents (TSC22D3). When pro-inflammatory cytokines are being controlled and reduced, a favorable environment can be created for healthy metabolism and reactions to occur.

FIG. 3A shows a decrease in mRNA gene activation for pro-inflammatory proteins as compared to the liquid portion alone, including the change in the mRNA expression for proteins acting as pro-inflammatory cytokines (CXCL1, CKCL8, IL1B, ILB6, TNFAIP2, TNFAIP3) or are involved in the pro-inflammatory response (BIRC3, ICAM1, NLRP10, PTX3). All pro-inflammatory genes are down-regulated, suggesting the creation of a less inflammatory environment for metabolic reactions to occur.

Figure 3B:
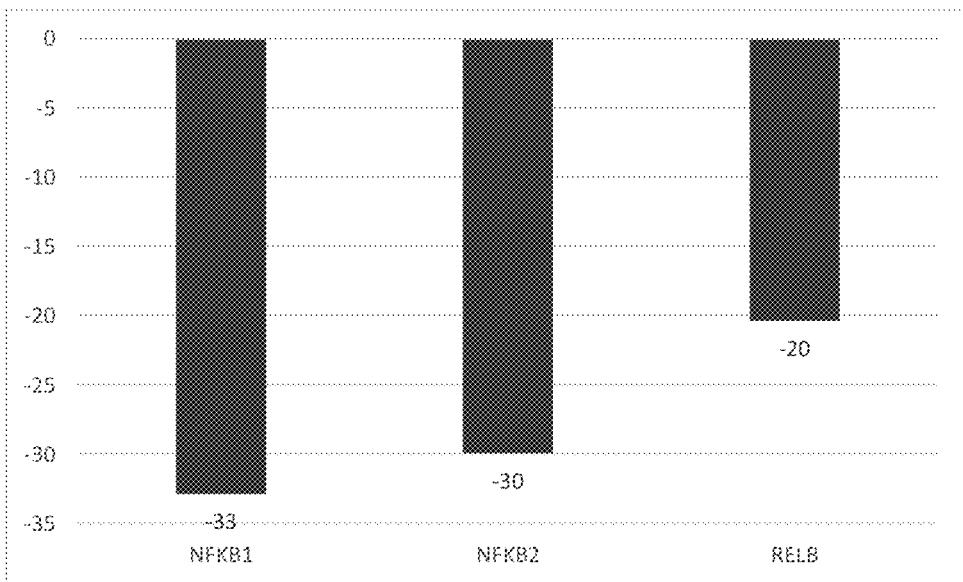

FIG. 3B shows the impact of the composition on the innate immune system. This figure shows the decrease in mRNA gene activation for key pro-inflammatory regulators as compared to the liquid portion alone, including the change in mRNA expression of key pro-inflammatory components. The master switch for the inflammation cascade/pathway includes the pro-inflammatory complex NF-kB. Components of this complex (RELB, NFKB1, NFKB2) are all downregulated, suggesting less inflammation activation through this pathway. This is similar to FIG. 3A, where pro-inflammatory cytokines are all downregulated as well.

Figure 3C:
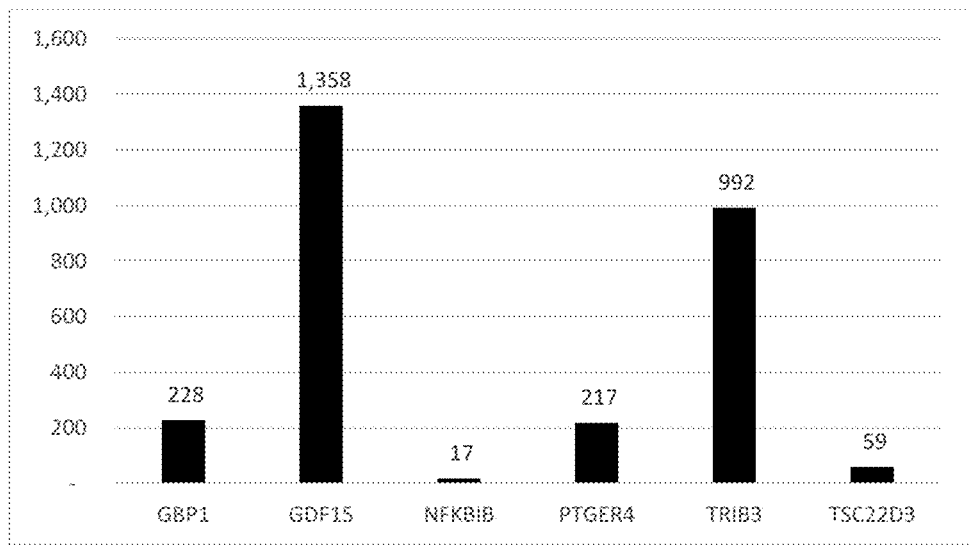

FIG. 3C shows the impact of the composition on the innate immune system. This figure shows increase in mRNA gene activation for key anti-inflammatory regulators as compared to the liquid portion alone, including the change in mRNA gene expression for proteins that are important anti-inflammatory components in reactions or are part of the anti-inflammatory pathways. Genes such as NFKBIB, TRIB3, and TSC22D3 either interfere with the assembly of the NF-kB complex or are transcriptional regulators that interfere with NF-kB activity. Other genes also restrain cellular proliferation in inflammatory contexts (GBP1) or are anti-inflammatory cytokines (PTGER4, GDF15). These effects help explain the results seen in FIG. 3B.

Figure 4:
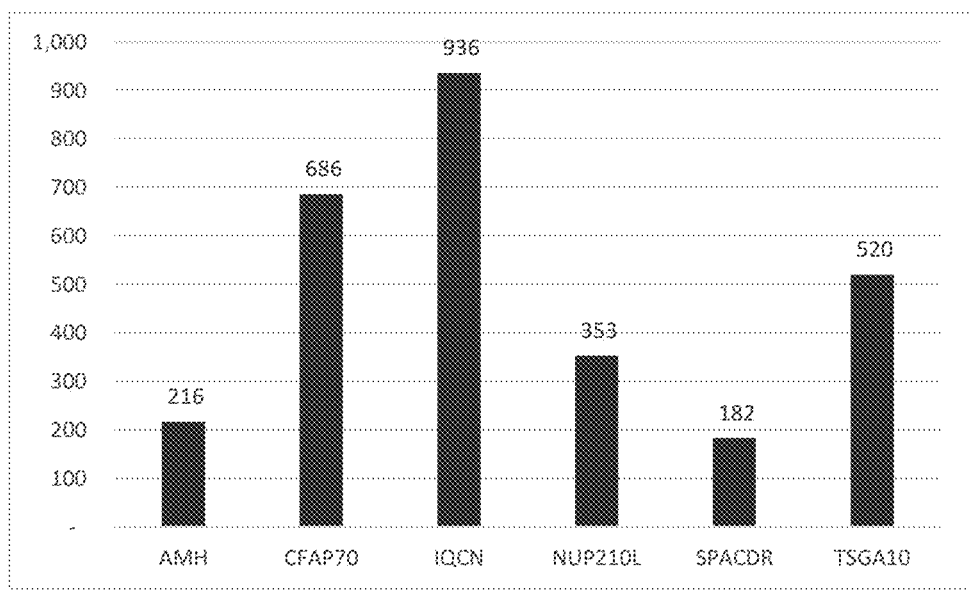
FIG. 4 shows the impact on male fertility of individuals ingesting some formulations of the compositions described herein.

FIG. 4 shows the impact of the combined portions of the composition on male fertility. This figure shows increase in mRNA gene activation for proteins involved in male fertility as compared to the liquid portion alone, including the change in mRNA gene expression in male sex differentiation and sperm health. Several genes are associated with sperm development and mobility (CFAP70, IQCN, SPACDR, TSGA10), sex differentiation during development (AMH), and testes health (NUP210L). FIG. 4 suggests healthier sperm development, mobility, and function based on the upregulation of genes that are involved with male fertility.

Figure 5:
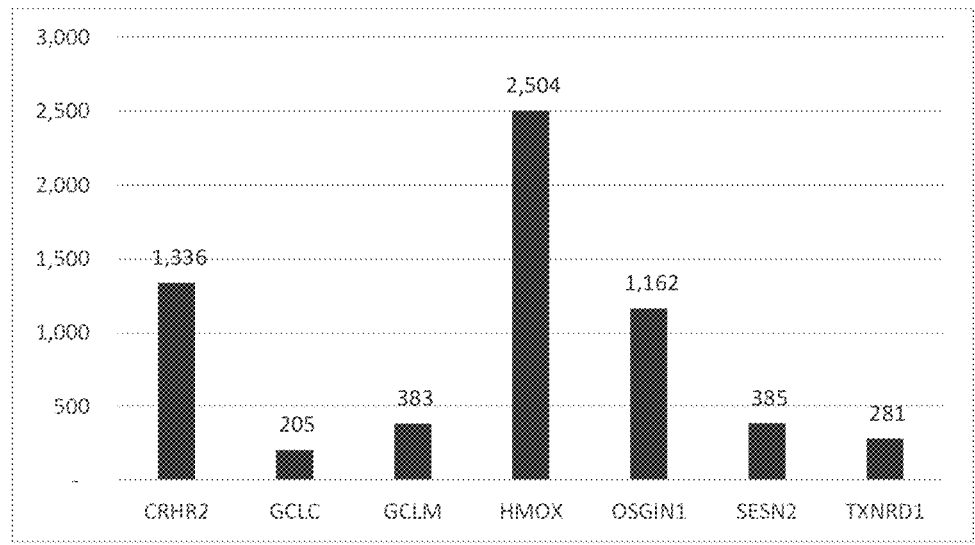
FIG. 5 shows the impact on the stress response of individuals ingesting some formulations of the compositions described herein.

FIG. 5 shows the impact of the composition on the stress response of the body. This figure shows an increase in mRNA gene activation for proteins involved in stress or antioxidant responses as compared to the liquid portion alone, including the change in mRNA gene expression for proteins involved in antioxidant response or production (GCLC, GCLM), oxidative stress (HMOX1, OSGIN1, TXNRD1), or general stress response (CRHR2, SESN2). This mRNA gene activation supports healthy antioxidative reactions to oxidative stress. Oxidative stress is an imbalance of the body's ability to readily counteract reactive oxygen species that are produced from chemical reactions occurring in biological systems, environmental influences, lifestyle, and more. Oxidative stress can result in DNA strand breaks, damage to cells, disruption in cellular signaling, and can contribute to aging and many diseases. The body has the ability to counteract this oxidative stress and respond to it appropriately. Biological systems are in place that initiate antioxidant response mechanisms to produce antioxidants such as glutathione, heme-oxygenase, and oxidoreductases, that fight oxidative stress. Another mechanism of the body induces proteins that regulate cell death so that cells damaged by oxidative stress or cancer cells are cleaned up and removed.

Figure 6:
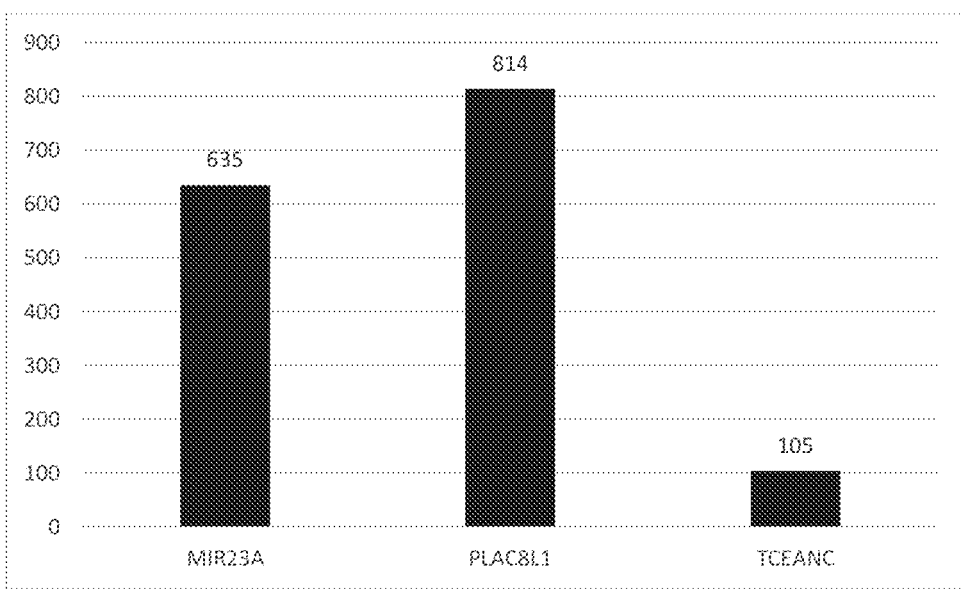
FIG. 6 shows the impact on DNA/RNA processes of individuals ingesting some formulations of the compositions described herein.

FIG. 6 shows the impact of the composition on DNA/RNA processes. This figure shows the changes in mRNA gene activation for proteins involved in DNA/RNA responses as compared to the liquid portion alone, including the change in mRNA gene expression of components that are part of healthy DNA function (PLAC8L1, TCEANC) or DNA responses (MIR23A). Healthy DNA allows for processing of healthy proteins that can function at optimal levels. DNA carries all the genetic information needed for all forms of life to grow, function, and reproduce. For genes to become proteins, lipids, or other components that tell the body how to function, they must go through a series of complicated reactions called transcription and translation, to get decoded and transported into the cell from the nucleus. Any damage to this mechanism must be repaired as soon as possible for healthy DNA responses to happen.

Figure 7:
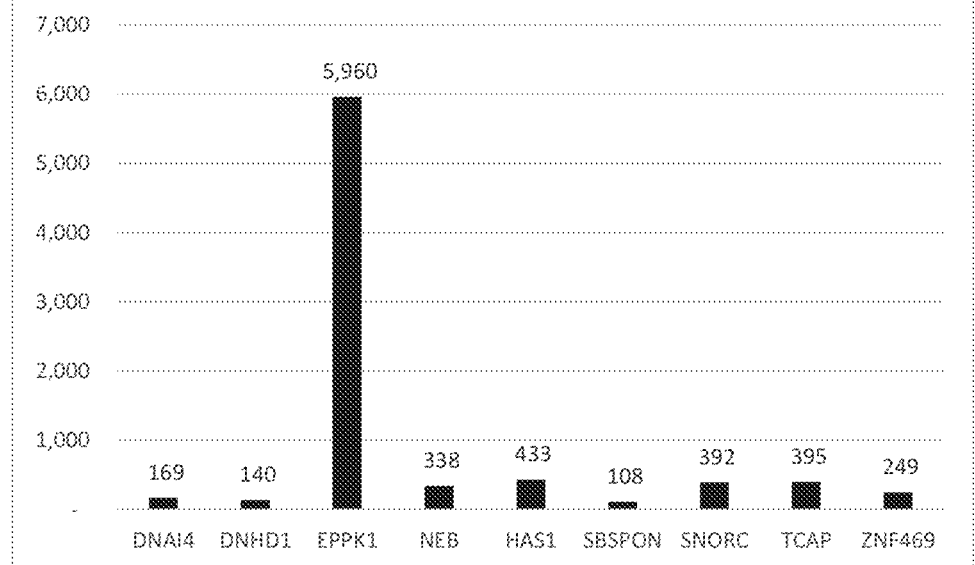
FIG. 7 shows the impact on structural proteins (e.g., skin, cartilage, membranes, muscle) of individuals ingesting some formulations of the compositions described herein.

FIG. 7 shows the impact of the composition on structural protein (e.g., skin, cartilage, membranes, muscle). This figure shows increases in mRNA gene activation for structural proteins found throughout the body as compared to the liquid portion alone, including the change in mRNA gene expression for proteins involved in structural development and homeostasis of structures. These genes are associated with skin integrity (EPPK1) and homeostasis (HAS1), cartilage development (SNORC), muscle protein assembly (NEB, TCAP), collagen fiber organization (ZNF469), and other structural proteins (DNAI4, DNHD1, SNSPON). These support the formation of collagen networks and other structural components of cells for further support of the pictures seen in FIGS. 1A-D. When organs in the body are compromised through physical or chemical injury, they have to be repaired. These proteins assist in telling the molecules how to assemble into an organized tissue network with a specific function since cells have to go through a maturation process to become specialized and active components of an organ.

The combination of the ingredients in the compositions produced several desirable results. First, they improved the appearance of fine lines and wrinkles, skin elasticity, skin tone and skin texture by influencing skin moisture, skin collagen density, and skin tone evenness. And second, the combination of ingredients showed a synergistic impact on key regulatory genes associated with several important cellular pathways, including the innate immune system (which deals directly with inflammatory responses to a disease or other insult to the body), the metabolism pathways (e.g., glucose metabolism, energy metabolism, structural cell integrity pathways), and the cellular pathways regulating male fertility development, stress responses and DNA transcription/replication processes. Activation of the genes involved in these pathways and processes addresses the bodily mechanisms that are involved in inflammation and the resulting diseases/issues.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative only and should not be construed to be limiting in any manner.

6. The composition of claim 1, wherein the composition contains about 50 ml of the second portion.

7. The composition of claim 1, wherein the second portion contains from about 1000 mg to about 10,000 mg fish collagen peptides.

8. The composition of claim 1, wherein the second portion contains from about 1000 mg to about 10,000 mg *formosa* ruby quinoa extract.

9. The composition of claim 1, wherein the second portion contains from about 1000 mg to about 10,000 mg of a lycopene-containing food source.

The invention claimed is:

1. A composition, comprising:
about 162.5 mg to about 2700 mg of a first portion, comprising:
   from about 150 mg to about 500 mg *Bacopa monnieri* extract having a least 20 weight percent bacosides;
   from about 225 mg to about 500 mg *Silybum marianum* extract having 70 weight percent to about 80 weight percent silymarin;
   from about 150 mg to about 500 mg *Withania somnifera* extract;
   from about 75 mg to about 500 mg *Camellia sinensis* extract comprised of at least 40 weight percent epigallocatechin gallate and about 98% polyphenols; and
   from about 75 mg to about 500 mg *Curcuma longa* extract comprised of at least about 95 weight percent curcumin; and
about 12.5 ml to about 100 ml of a second portion, comprising:
   from about 500 mg to about 15,000 mg fish collagen peptides comprising about 90 weight percent protein; and
   from about 500 mg to about 15,000 mg *formosa* ruby quinoa mixture containing about 10 wt % extract and about 90 wt % water.

2. The composition of claim 1, wherein the first portion is a solid and the second portion is a liquid.

3. The composition of claim 1, wherein the composition contains from about 325 mg to about 1350 mg of the first portion.

4. The composition of claim 1, wherein the composition contains from about 25 ml to about 75 ml of the second portion.

5. The composition of claim 1, wherein the composition contains about 675 mg of the first portion.

10. The composition of claim 1, wherein the second portion contains from about 50 mg to about 1000 mg of an herbal combination of young ponkan fruit and blueberry powder.

11. A nutritional supplement, comprising:
about 325 mg to about 1350 mg of a solid portion, comprising:
   from about 150 mg to about 500 mg *Bacopa monnieri* extract having a least 20 weight percent bacosides;
   from about 225 mg to about 500 mg *Silybum marianum* extract having 70 weight percent to about 80 weight percent silymarin;
   from about 150 mg to about 500 mg *Withania somnifera* extract;
   from about 75 mg to about 500 mg *Camellia sinensis* extract, wherein said green tea extract is comprised of at least 40 weight percent epigallocatechin gallate and about 98% polyphenols; and
   from about 75 mg to about 500 mg *Curcuma longa* extract, wherein said turmeric extract is comprised of at least about 95 weight percent curcumin; and
about 25 ml to about 75 ml of a liquid portion, comprising:
   from about 500 mg to about 15,000 mg fish collagen peptides comprising about 90 weight percent protein; and
   from about 500 mg to about 15,000 mg *formosa* ruby quinoa mixture containing about 10 wt % extract and about 90 wt % water.

12. The composition of claim 11, wherein the composition contains about 675 mg of the first portion.

13. The composition of claim 11, wherein the composition contains about 50 ml of the second portion.

14. The composition of claim 11, wherein the second portion contains from about 1000 mg to about 10,000 mg fish collagen peptides.

15. The composition of claim 11, wherein the second portion contains from about 1000 mg to about 10,000 mg *formosa* ruby quinoa extract.

16. The composition of claim 11, wherein the liquid portion further comprises about 1000 mg to about 10,000 mg of a lycopene-containing food source.

17. The composition of claim 11, wherein the liquid portion further comprises about 50 mg to about 1000 mg of an herbal combination of young ponkan fruit and blueberry powder.

18. A method of improving the skin condition of an individual comprising administering to that individual a composition comprising:

about 675 mg of a solid portion, comprising:

about 150 mg *Bacopa monnieri* extract having a least 20 weight percent bacosides;

about 225 mg *Silybum marianum* extract having 70 weight percent to about 80 weight percent silymarin;

about 150 mg *Withania somnifera* extract;

about 75 mg *Camellia sinensis* extract, wherein said green tea extract is comprised of at least 40 weight percent epigallocatechin gallate and about 98% polyphenols; and about 75 mg *Curcuma longa* extract, wherein said turmeric extract is comprised of at least about 95 weight percent curcumin; and about 50 ml of a liquid portion, comprising:

about 5000 mg fish collagen peptides comprising about 90 weight percent protein; and about 5000 mg *formosa* ruby quinoa mixture containing about 10 wt % extract and about 90 wt % water.

19. The method of claim 18, wherein the composition is administered to the individual for at least 30 days or more.

20. A method of activating cellular signaling genes in innate inflammatory pathways, comprising administering to an individual a composition comprising:

about 675 mg of a solid portion, comprising:

about 150 mg *Bacopa monnieri* extract having a least 20 weight percent bacosides;

about 225 mg *Silybum marianum* extract having 70 weight percent to about 80 weight percent silymarin;

about 150 mg *Withania somnifera* extract;

about 75 mg *Camellia sinensis* extract, wherein said green tea extract is comprised of at least 40 weight percent epigallocatechin gallate and about 98% polyphenols; and about 75 mg *Curcuma longa* extract, wherein said turmeric extract is comprised of at least about 95 weight percent curcumin; and about 50 ml of a liquid portion, comprising:

about 5000 mg fish collagen peptides comprising about 90 weight percent protein; and about 5000 mg *formosa* ruby quinoa mixture containing about 10 wt % extract and about 90 wt % water.

21. The method of claim 20, wherein the composition is administered to the individual for at least 30 days or more.

\* \* \* \* \*